(12) United States Patent
Von Arx et al.

(10) Patent No.: US 7,060,030 B2
(45) Date of Patent: Jun. 13, 2006

(54) TWO-HOP TELEMETRY INTERFACE FOR MEDICAL DEVICE

(75) Inventors: Jeffrey A. Von Arx, Minneapolis, MN (US); Michael J. Lyden, Shoreview, MN (US); William J. Linder, Golden Valley, MN (US); Scott T. Mazar, Inver Grove Heights, MN (US); Allan T. Koshiol, Lino Lakes, MN (US); Mark Gryzwa, Woodbury, MN (US); Dorothy Nauman, Stillwater, MN (US); Scott Hostine, Woodbury, MN (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 434 days.

(21) Appl. No.: 10/041,725

(22) Filed: Jan. 8, 2002

(65) Prior Publication Data

US 2003/0130708 A1    Jul. 10, 2003

(51) Int. Cl.
*A61B 5/00* (2006.01)
(52) U.S. Cl. .................................. 600/300
(58) Field of Classification Search ............. 128/901, 128/903; 340/539.12, 572.7, 573.1, 539.32; 343/724, 749, 750, 860, 861; 607/30–33, 607/60, 61, 9, 14; 375/240; 455/462; 600/300, 600/373–377
See application file for complete search history.

(56) References Cited

U.S. PATENT DOCUMENTS

| | | | |
|---|---|---|---|
| 3,843,896 A | 10/1974 | Rason et al. | 310/4 |
| 3,846,704 A | 11/1974 | Bessette | 325/66 |
| 4,266,551 A * | 5/1981 | Stein | 607/9 |
| 4,556,063 A * | 12/1985 | Thompson et al. | 607/32 |
| 4,918,690 A | 4/1990 | Markkula, Jr. et al. | 370/400 |
| 4,941,143 A | 7/1990 | Twitty et al. | 370/445 |
| 4,947,484 A | 8/1990 | Twitty et al. | 714/776 |
| 4,955,018 A | 9/1990 | Twitty et al. | 370/398 |
| 4,969,146 A | 11/1990 | Twitty et al. | 370/388 |
| 5,034,882 A | 7/1991 | Eisenhard et al. | 712/30 |
| 5,113,869 A | 5/1992 | Nappholz et al. | 128/696 |

(Continued)

FOREIGN PATENT DOCUMENTS

EP        515059         11/1992

(Continued)

OTHER PUBLICATIONS

Carlson, Gerrard M., et al., "Cardiac Rhythm Management System Using Time-Domain Heart Rate Variability Indicia", U.S. Appl. No. 10/726,062, Filed Dec. 2, 2003, 42 pgs.

*Primary Examiner*—George Manuel
(74) *Attorney, Agent, or Firm*—Schwegman, Lundberg, Woessner & Kluth, P.A.

(57) ABSTRACT

This document discusses a system that includes an intermediary telemetry interface device for communicating between a cardiac rhythm management system or other implantable medical device and a programmer or other remote device. One example provides an inductive near-field communication link between the telemetry interface and the implantable medical device, and a radio-frequency (RF) far-field communication link between the telemetry interface device and the remote device. The telemetry interface device provides data buffering. In another example, the telemetry interface device includes a data processing module for compressing and/or decompressing data, or for extracting information from data. Such information extraction may include obtaining heart rate, interval, and/or depolarization morphology information from an electrogram signal received from the implantable medical device.

38 Claims, 4 Drawing Sheets

U.S. PATENT DOCUMENTS

| | | | |
|---|---|---|---|
| 5,199,429 A | 4/1993 | Kroll et al. | 607/5 |
| 5,348,008 A | 9/1994 | Bornn et al. | 600/301 |
| 5,383,915 A | 1/1995 | Adams | 607/60 |
| 5,507,781 A | 4/1996 | Kroll et al. | 607/7 |
| 5,564,429 A | 10/1996 | Bornn et al. | 600/508 |
| 5,592,512 A * | 1/1997 | Spiess | 375/240 |
| 5,626,630 A | 5/1997 | Markowitz et al. | 607/60 |
| 5,720,770 A | 2/1998 | Nappholz et al. | 607/30 |
| 5,752,976 A * | 5/1998 | Duffin et al. | 607/32 |
| 5,807,397 A * | 9/1998 | Barreras | 607/61 |
| 5,930,719 A * | 7/1999 | Babitch et al. | 455/462 |
| 6,073,046 A | 6/2000 | Patel et al. | 600/509 |
| 6,083,248 A | 7/2000 | Thompson | 607/30 |
| 6,243,606 B1 * | 6/2001 | Mann et al. | 607/14 |
| 6,266,554 B1 | 7/2001 | Hsu et al. | 600/515 |
| 6,272,377 B1 | 8/2001 | Sweeney et al. | 600/515 |
| 6,272,379 B1 | 8/2001 | Fischell et al. | 607/5 |
| 6,275,732 B1 | 8/2001 | Hsu et al. | 607/14 |
| 6,347,245 B1 | 2/2002 | Lee et al. | 600/523 |
| 6,434,429 B1 | 8/2002 | Kraus et al. | 607/60 |
| 6,544,171 B1 | 4/2003 | Beetz et al. | 600/300 |
| 6,553,262 B1 | 4/2003 | Lang et al. | 607/32 |
| 6,558,320 B1 | 5/2003 | Causey, II et al. | 600/300 |
| 6,574,510 B1 * | 6/2003 | Von Arx et al. | 607/60 |
| 6,641,533 B1 | 11/2003 | Causey, II et al. | 600/300 |
| 6,650,944 B1 | 11/2003 | Goedeke et al. | 607/60 |
| 6,675,049 B1 | 1/2004 | Thompson et al. | 607/60 |
| 6,678,547 B1 | 1/2004 | Carlson et al. | 600/515 |
| 6,738,671 B1 | 5/2004 | Christophersom et al. | 607/60 |
| 2002/0002326 A1 | 1/2002 | Causey, III et al. | 600/300 |
| 2002/0026122 A1 | 2/2002 | Lee et al. | 600/523 |
| 2002/0045804 A1 | 4/2002 | Christopherson et al. | 600/300 |
| 2002/0072783 A1 | 6/2002 | Goedeke et al. | 607/60 |
| 2002/0123672 A1 | 9/2002 | Christophersom et al. | 600/300 |
| 2002/0193846 A1 | 12/2002 | Pool et al. | 607/60 |
| 2003/0018369 A1 | 1/2003 | Thompson et al. | 607/60 |
| 2003/0078631 A1 | 4/2003 | Nelson | 607/30 |
| 2003/0088290 A1 * | 5/2003 | Spinelli et al. | 607/30 |
| 2003/0093187 A1 | 5/2003 | Walker | 701/1 |
| 2003/0139778 A1 | 7/2003 | Fischell et al. | 607/3 |
| 2003/0149423 A1 | 8/2003 | Fischell et al. | 604/892.1 |
| 2003/0163173 A1 | 8/2003 | Lindberg et al. | 607/60 |
| 2003/0216793 A1 | 11/2003 | Karlsson et al. | 607/60 |
| 2003/0221118 A1 | 11/2003 | Walker | 713/193 |
| 2003/0233129 A1 | 12/2003 | Matos | 607/5 |
| 2004/0030365 A1 | 2/2004 | Rubin | 607/60 |
| 2004/0073095 A1 | 4/2004 | Causey, III et al. | 600/300 |
| 2004/0078067 A1 | 4/2004 | Thompson et al. | 607/60 |
| 2004/0116981 A1 | 6/2004 | Mazar | 607/60 |
| 2004/0117204 A1 | 6/2004 | Mazar et al. | 705/2 |
| 2004/0122488 A1 | 6/2004 | Mazar et al. | 607/60 |
| 2004/0122489 A1 | 6/2004 | Mazar et al. | 607/60 |
| 2004/0127802 A1 | 7/2004 | Istvan et al. | 600/509 |
| 2004/0128161 A1 | 7/2004 | Mazar et al. | 705/2 |
| 2004/0176822 A1 | 9/2004 | Thompson et al. | 607/50 |

FOREIGN PATENT DOCUMENTS

| | | |
|---|---|---|
| EP | 1062984 | 12/2000 |
| EP | 1340519 | 9/2003 |
| EP | 1362614 | 11/2003 |
| WO | WO-8904517 | 5/1989 |
| WO | WO-8904521 | 5/1989 |
| WO | WO-8904578 | 5/1989 |
| WO | WO-9611722 | 4/1996 |
| WO | WO-9936297 | 7/1999 |
| WO | WO-9955227 | 11/1999 |
| WO | WO-0078057 | 12/2000 |
| WO | WO-0119239 | 3/2001 |
| WO | WO-0145793 | 6/2001 |
| WO | WO-0152727 | 7/2001 |
| WO | WO-0156467 | 8/2001 |
| WO | WO-0184274 | 11/2001 |
| WO | WO-0234331 | 5/2002 |
| WO | WO-02045798 | 6/2002 |
| WO | WO-03008037 | 1/2003 |
| WO | WO-03029922 | 4/2003 |
| WO | WO-03061465 | 7/2003 |
| WO | WO-03072192 | 9/2003 |
| WO | WO-03103765 | 12/2003 |
| WO | WO-04056301 | 7/2004 |

* cited by examiner

TWO-HOP TELEMETRY INTERFACE FOR MEDICAL DEVICE

TECHNICAL FIELD

This document relates generally to medical systems, devices, and methods, and particularly, but not by way of limitation, to a two-hop telemetry interface for a medical device such as an implantable cardiac rhythm management device.

BACKGROUND

When functioning properly, the human heart maintains its own intrinsic rhythm. Its sinoatrial node generates intrinsic electrical cardiac signals that depolarize the atria, causing atrial heart contractions. Its atrioventricular node then passes the intrinsic cardiac signal to depolarize the ventricles, causing ventricular heart contractions. These intrinsic cardiac signals can be sensed on a surface electrocardiogram (ECG) obtained from electrodes placed on the patient's skin, or from electrodes implanted within the patient's body. The surface ECG waveform, for example, includes artifacts associated with atrial depolarizations ("P-waves") and those associated with ventricular depolarizations ("QRS complexes").

A normal heart is capable of pumping adequate blood throughout the body's circulatory system. However, some people have irregular cardiac rhythms, referred to as cardiac arrhythmias. Moreover, some patients have poorly spatially-coordinated heart contractions. In either case, diminished blood circulation may result. For such patients, a cardiac rhythm management system may be used to improve the rhythm and/or spatial coordination of heart contractions. Such systems are often implanted in the patient and deliver therapy to the heart.

Cardiac rhythm management systems include, among other things, pacemakers, also referred to as pacers. Pacers deliver timed sequences of low energy electrical stimuli, called pace pulses, to the heart, such as via an intravascular leadwire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly. Such pacers may also coordinate atrial and ventricular contractions to improve pumping efficiency. Cardiac rhythm management systems also include cardiac resynchronization therapy (CRT) devices for coordinating the spatial nature of heart depolarizations for improving pumping efficiency. For example, a CRT device may deliver appropriately timed pace pulses to different locations of the same heart chamber to better coordinate the contraction of that heart chamber, or the CRT device may deliver appropriately timed pace pulses to different heart chambers to improve the manner in which these different heart chambers contract together.

Cardiac rhythm management systems also include defibrillators that are capable of delivering higher energy electrical stimuli to the heart. Such defibrillators include cardioverters, which synchronize the delivery of such stimuli to portions of sensed intrinsic heart activity signals. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering a high energy electrical stimulus that is sometimes referred to as a defibrillation countershock, also referred to simply as a "shock." The countershock interrupts the tachyarrhythmia, allowing the heart to reestablish a normal rhythm for the efficient pumping of blood. In addition to pacers, CRT devices, and defibrillators, cardiac rhythm management systems also include devices that combine these functions, as well as monitors, drug delivery devices, and any other implantable or external systems or devices for diagnosing or treating the heart.

One problem faced by cardiac rhythm management devices and other implantable medical devices is in providing communication (i.e., telemetry) between the implanted device and a remote external interface device. The external interface device may be a dedicated or other programmer device used by a physician or other caregiver to interface with the implanted device. Such a bidirectional communication link permits, among other things, programming of operational parameter(s) and/or executable code within the implanted device, and/or monitoring of device status indicator(s) and/or patient data. The present inventors have recognized that a long telemetry range is desired so that the physician or caregiver may, if desired, access the implanted device from a remote location. However, using a far-field radio frequency (RF) communication link from an implanted medical device consumes significant power from the battery or other power source of the implanted medical device. This shortens the useful life of the implanted medical device before explantation and replacement becomes necessary. Moreover, a far-field RF signal transceived from an implanted location within the body faces significant absorption of the transceived power by body tissue. This further increases the power required to obtain long range telemetry transception. For these and other reasons, the present inventors have recognized that there exists an unmet need for improved techniques of providing long-range telemetry using less power from the power source of the implanted device.

SUMMARY

This document discusses, among other things, a system, method, or device that includes an intermediary telemetry interface device for communicating between a cardiac rhythm management system or other implantable medical device and a programmer or other remote device. One example provides an inductive near-field communication link between the telemetry interface and the implantable medical device, and a far-field radio-frequency (RF) far-field communication link between the telemetry interface device and the remote device. The telemetry interface device provides data buffering. In another example, the telemetry interface device includes a data processing module, such as for compressing and/or decompressing data, or for extracting information from data. Such information extraction may include obtaining heart rate, interval, and/or depolarization morphology information from an electrogram signal received from the implantable medical device.

In one example, this document discusses an external telemetry interface device to assist in communication between an implantable medical device carrying an inductive element and an external remote first far-field radio-frequency (RF) transceiver. The telemetry interface device includes an inductive transceiver, configured to be communicatively coupled to the inductive element in the implantable medical device via a mutual inductance therebetween. It also includes a second far-field RF transceiver, configured to be communicatively coupled to the remote first far-field RF transceiver. It further includes a data buffer, coupled to the inductive and second far-field RF transceivers, to store data from the inductive and second far-field RF transceivers. Moreover, the telemetry interface device includes a controller, coupled to the inductive and second far-field RF transceivers and the data buffer, to issue control signals directing communication by the inductive and second far-field RF transceivers using data from the data buffer.

In another example, this document discusses an external telemetry interface device to assist in communication between an implantable medical device and a remote far-field radio-frequency (RF) transceiver. The telemetry interface device includes a first transceiver, configured to be communicatively coupled to the implantable medical device. It includes a second transceiver, configured to be communicatively coupled to the remote far-field RF transceiver. It also includes a data buffer, coupled to the first and second transceivers, to store data from the first and second transceivers. It further includes a controller, coupled to the first and second transceivers and the data buffer, to issue control signals directing communication by the first and second transceivers using data from the data buffer. The controller includes a data processing module. The data processing module is configured to execute instructions to obtain extracted information, from electrogram data received from the implanted device via the first transceiver, for transmission by the second transceiver to the remote far-field RF transceiver.

This document also discusses a method of communicating between an implantable medical device and an external remote far-field RF transceiver. The method includes transceiving with the implantable medical device an inductively-coupled first communication signal. The method also includes transceiving with the external remote far-field RF receiver a second communication signal. The method also includes buffering data received from at least one of the first and second communication signals.

This document also discusses a method of communicating between an implantable medical device and an external remote far-field RF transceiver. The method includes transceiving with the implantable medical device a first communication signal. It also includes extracting information from electrogram data included in the first communication signal. It further includes transceiving with the external remote far-field RF receiver a second communication signal. Other aspects of the invention will be apparent on reading the following detailed description of the invention and viewing the drawings that form a part thereof.

BRIEF DESCRIPTION OF THE DRAWINGS

In the drawings, which are offered by way of example, and not by way of limitation, and which are not necessarily drawn to scale, like numerals describe substantially similar components throughout the several views. Like numerals having different letter suffixes represent different instances of substantially similar components.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents.

Figure 1:
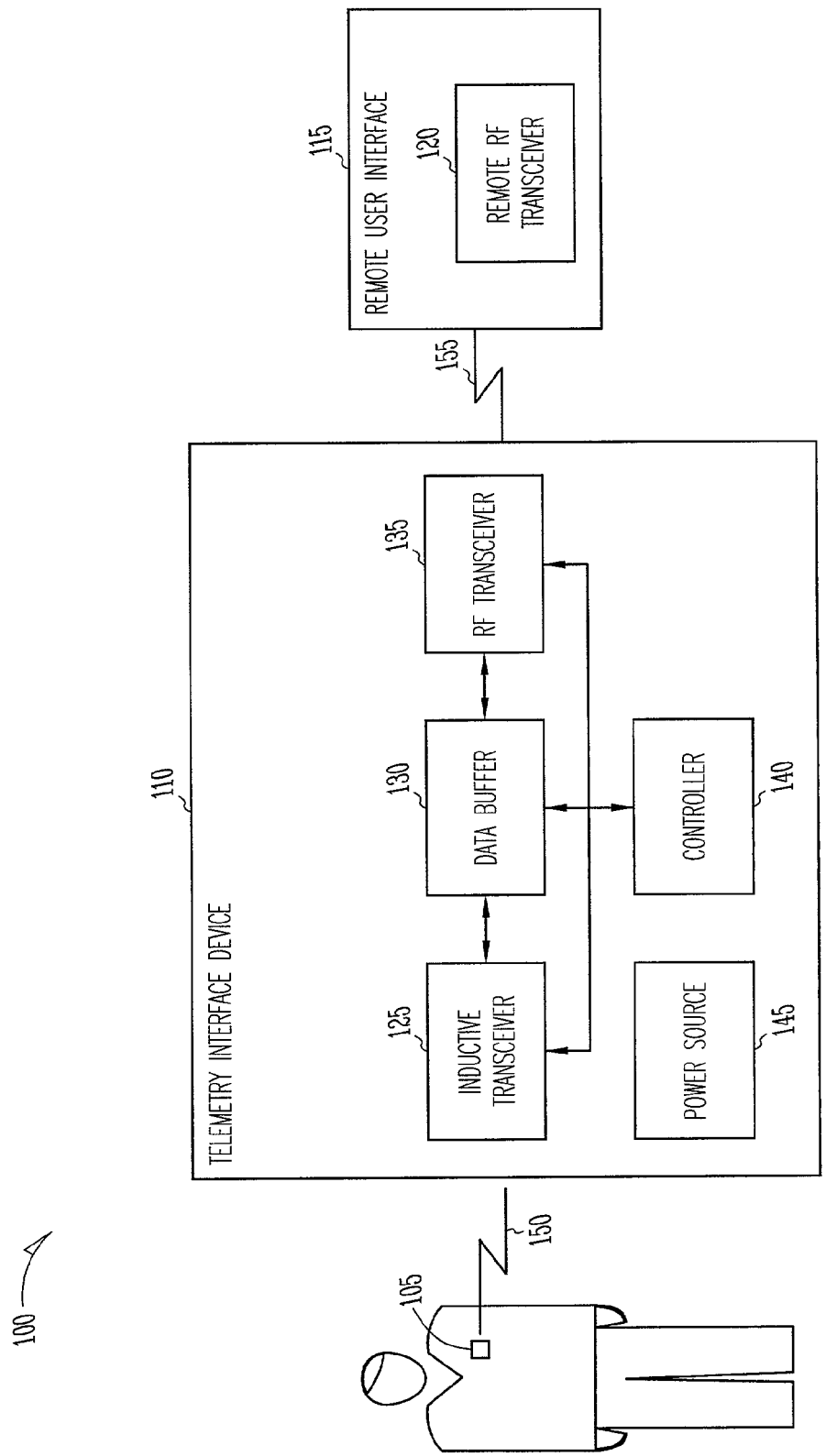
FIG. 1 is a block diagram illustrating generally portions of a system including an implantable medical device, an external telemetry interface (I/F) device, and a remote user interface device.

FIG. 1 is a block diagram illustrating generally portions of a system 100 including an implantable medical device 105 (such as a cardiac rhythm management device), an external telemetry interface (I/F) device 110, and a remote user interface device 115 (such as a programmer and/or monitor for use with the implantable medical device 105) that includes a remote far-field radio-frequency (RF) transceiver 120. In this document, the terms "transceive," "transceiving," and "transceiver" refer to transmitting and/or receiving data. That is, these terms include all of: (1) transmitting, but not receiving; (2) receiving, but not transmitting; and, (3) both transmitting and receiving. Moreover, a "far-field," which is also referred to as the Fraunhofer zone, refers to the zone in which a component of an electromagnetic field produced by the transmitting electromagnetic radiation source decays substantially proportionally to 1/r, where r is the distance between an observation point and the radiation source. Accordingly, far-field refers to the zone outside the boundary of $r=\lambda/2\pi$, where $\lambda$ is the wavelength of the transmitted electromagnetic energy. In one example, far-field RF telemetry is capable of communicating over a range that is at least six feet, but far-field RF communication may extend over a far greater distance.

In the example of FIG. 1, telemetry IF device 110 includes an inductive transceiver 125, a random-access memory (RAM) or other data buffer 130, a far-field RF transceiver 135, a controller 140, and a power source 145 (such as a rechargeable or other battery). In this example, inductive transceiver 125 is wirelessly communicatively coupled by near-field link 150 to implantable medical device 105, using the mutual inductance coupling respective coils or other inductors. Far-field RF transceiver 135 is wirelessly communicatively coupled to remote user interface 115, using radiated far-field RF electromagnetic energy transmitted between respective antennas by far-field communication link 155. Because communication of data signals at links 150 and 155 may occur at different rates and/or may not be carried out concurrently, data buffer 130 performs data buffering in at least one direction, as directed by one or more control signals provided by controller 140. Controller 140 is capable of sequencing through various control states such as, for example, by using a digital microprocessor having executable instructions stored in an associated instruction memory circuit, a microsequencer, or a state machine.

Telemetry interface device 110 may be worn or otherwise kept in close proximity to a patient in which implantable medical device 105 is implanted. In one example, telemetry interface device 110 is housed in an enclosure that fits in the patient's pocket or can be worn on a belt. Remote user interface 115 may be close to the patient (e.g., in the same room), or may be located at an extended distance from the patient. Far-field communication link 155 uses far-field RF energy, for example, at one or more ISM band frequencies (e.g., about 902 MHz to 928 MHz), ISM/BLUETOOTH frequencies (e.g., about 2.4 GHz to 2.5 GHz), cell phone band frequencies (e.g., Advanced Mobile Phone System (AMPS) at about 824 MHz to 894 MHz, Personal Communication Services (PCS) at about 1.8 GHz to 2.0 GHz, etc.), two-way pager band frequencies (e.g., 930 MHz to 950 MHz), and/or Global System for Mobile (GSM) frequencies at about 1.85 GHz to 1.99 GHz. Far-field communication link 155 uses a mutual inductance coupling implantable device 105 to telemetry interface device 110. This configuration of system 100 advantageously permits implantable device 105 to also communicate, using a mutual inductance, to an existing inductively-coupled implantable medical device programmer, as well as to telemetry interface device 110.

Figure 2:
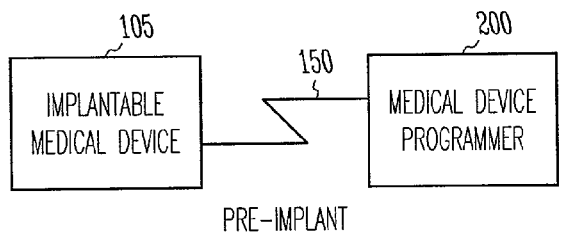
FIG. 2 illustrates a technique of communication between an implantable medical device and a conventional medical device programmer using a near-field inductive communication link.

FIG. 2 illustrates a technique of communication between implantable medical device 105 and a conventional medical device programmer 200 (before device 105 is implanted in a patient), using near-field inductive communication link 150. For example, such communication may be used to program parameters of implantable medical device 105 using a user-interface of programmer 200. In another example, such communication may be used to obtain device status information at programmer 200 from implantable medical device 105.

Figure 3:
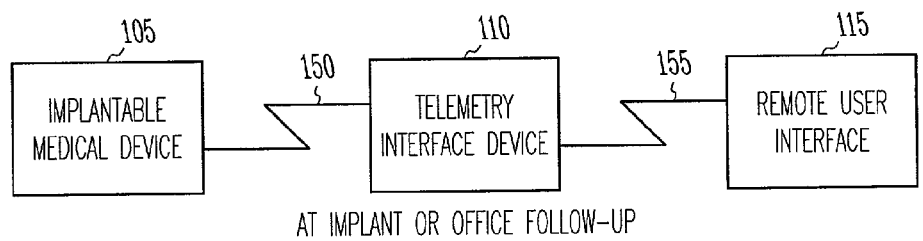
FIG. 3 illustrates a technique of communication between an implantable medical device and a remote user interface via a telemetry interface device.

FIG. 3 illustrates a technique of far-field RF communication between implantable medical device 105 and remote user interface 115 (such as, for example, a medical device programmer 200 having both far-field RF and inductive transceiver capabilities), via telemetry interface device 110. Implantable medical device 105 and telemetry interface device 110 are communicatively linked by near-field inductive communication link 150. Telemetry interface device 110 and remote user interface 115 are communicatively linked by far-field RF communication link 155. In one example, such communication occurs during or immediately after the implantation of implantable medical device 105 into a patient, or during a subsequent follow-up visit by the patient to the doctor or other care-giver.

Figure 4:
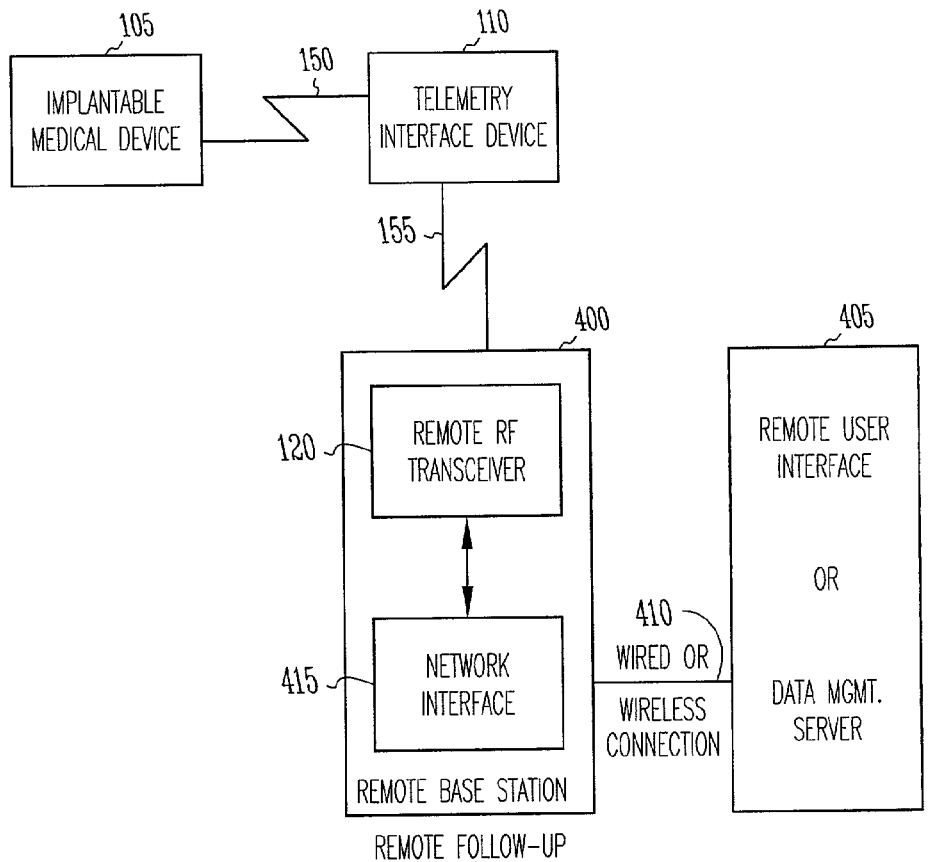
FIG. 4 illustrates a technique of communication: (1) between an implantable medical device and a telemetry interface device, using a near-field inductive communication link; (2) between a telemetry interface device and a remote base station, using a far-field RF communication link; and (3) between a remote base station and a remote user interface, using a wired or wireless communication link.

FIG. 4 illustrates a technique of communication: (1) between implantable medical device 105 and telemetry interface device 110, using a near-field inductive communication link 150; (2) between telemetry interface device 110 and remote base station 400, using a far-field RF communication link 155; and (3) between remote base station 400 and a remote user interface (or data management server) 405, using a wired communication link 410 (e.g., telephone lines, internet connection, etc.) or a wireless communication link (e.g., cell phone link, far-field RF link, etc.). In this example, remote base station 400 includes a remote far-field RF transceiver 120 and a network interface 415 coupled thereto. Network interface 415 includes a modem or other suitable device that is adapted for communication over the wired or wireless communication link 410. Remote user interface 405 may include a medical device programmer 200, operated by a doctor or other care-giver. Alternatively, remote user interface 405 may include a data management server for storing physiological data, device status data, or other data received from implantable medical device 105, or for automatically providing programmable parameters to configure implantable medical device 105.

Figure 5:
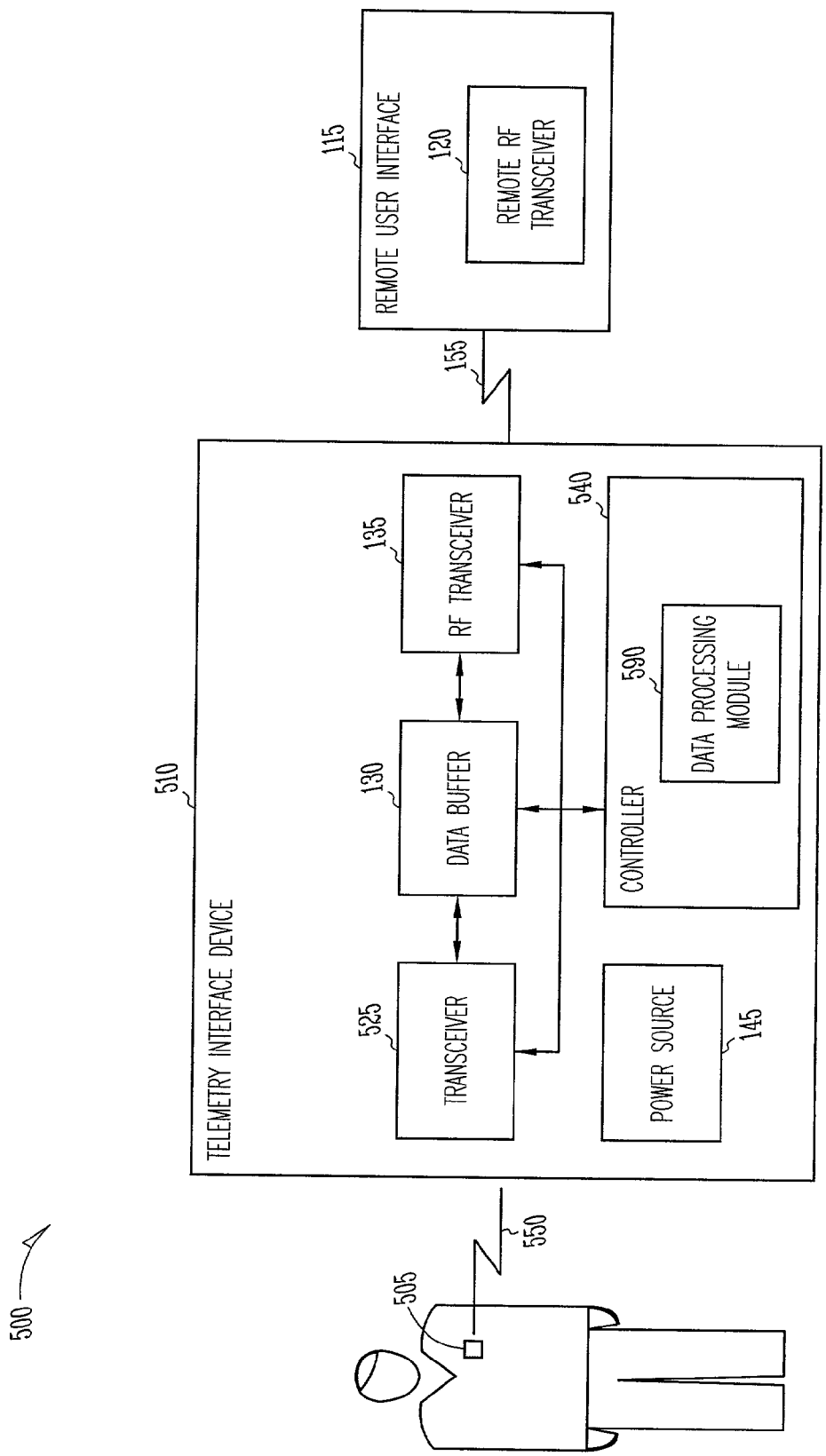
FIG. 5 is a block diagram illustrating generally portions of an alternative system including an implantable medical device, an external telemetry interface (I/F) device, and a remote user interface device.

FIG. 5 is a block diagram illustrating generally portions of an alternative system 500 including an implantable medical device 505, an external telemetry interface (I/F) device 510, and a remote user interface device 115 (such as a programmer and/or monitor for use with the implantable medical device 505) that includes a remote far-field radio-frequency (RF) transceiver 120. In the example of FIG. 5, telemetry IF device 510 includes a far-field RF or an inductive transceiver 525, a random-access memory (RAM) or other data buffer 130, a far-field RF transceiver 135, a controller 540, and a power source 145. In this example, transceiver 525 is wirelessly communicatively coupled by far-field RF or near-field inductive communication link 550 to implantable medical device 505. Far-field RF transceiver 135 is wirelessly communicatively coupled to remote user interface 115, using radiated far-field RF electromagnetic energy transmitted between respective antennas by far-field link 155. Because data communication at links 550 and 155 may occur at different rates and/or may not be carried out concurrently, data buffer 130 performs data buffering in at least one direction, as directed by one or more control signals provided by controller 540.

Controller 540 includes a data processing module 590. In one example, data processing module 590 performs executable steps for compressing and/or decompressing data being buffered in data buffer 130 for communication to and/or from implantable medical device 505. In one such example, telemetry interface device 510 receives physiological data (e.g., an cardiac signal electrogram) over an extended period of time, and data processing module 590 uses Huffman encoding or another suitable data compression technique to compress the data before communicating it to remote user interface 115.

In another example, communication at link 550 operates using a high efficiency communication protocol tailored for communication with implantable device 505. In this example, data processing module 590 translates the data from implantable device 505, as needed, to enable far-field RF communication at far-field communication link 155 using a standardized communication protocol. In this example, such processing by data processing module 590 may include stripping a header on data received from implantable device 505 over link 550, and adding a TCP/IP or other standardized header to data being communicated over far-field RF communication link 155 to remote user interface 115.

In one example, device 505 occasionally or periodically transmits, to telemetry interface device 510, physiological information, such as electrogram information about one or more cardiac signals sensed at one or more patient electrodes. Data processing module 590 includes a level-detection or other suitable algorithm for detecting cardiac depolarizations included in the cardiac signal. Using this extracted information about heart depolarizations, data processing module 590 calculates average heart rate, the values of the time intervals between successive heart depolarizations, and/or morphology information about the depolarizations. Other processing by data processing module 590 may include, among other things: calculating heart rate variability (e.g., for diagnosing patient wellness), recognizing and/or classifying an arrhythmia (e.g., atrial flutter, atrial fibrillation, etc.) or other characteristic of the cardiac signal (e.g., QT alternans, etc.). Such processing may also include a comparison of a characteristic to a threshold value, or any other suitable technique for generating an alert condition that is communicated to a physician or other caregiver at remote user interface 115, using far-field RF communication link 155.

Such information extracted from the heart depolarizations is then transmitted by far-field RF transceiver 135 to remote user interface 115 via far-field RF communication link 155, as an alternative to transmitting all of the source electrogram data. Examples of extracting depolarization morphology information are found in Hsu et al. U.S. Pat. No. 6,275,732 entitled MULTIPLE STAGE MORPHOLOGY BASED SYSTEM DETECTING VENTRICULAR TACHYCARDIA AND SUPRAVENTRICULAR TACHYCARDIA and Hsu et al. U.S. Pat. No. 6,266,554 entitled SYSTEM AND METHOD FOR CLASSIFYING CARDIAC COMPLEXES, each of which is assigned to Cardiac Pacemakers, Inc., and each of which is incorporated by reference herein in its entirety, including its description of using cardiac features and/or morphology information.

In another example in which device 505 regularly transmits to telemetry interface device 510 physiological information (e.g., electrogram information about one or more cardiac signals sensed at one or more patient electrodes, and/or information from one or more physiological sensors such as an accelerometer, a minute ventilation sensor, etc.), telemetry interface device 510 processes the physiological data to compute one or more indicators of patient wellness, which are then transmitted by far-field RF transceiver 135 to remote user interface 115 via far-field RF communication link 155. One example of processing physiological and/or sensor data to determine an indicator of patient wellness is described in Carlson et al. U.S. patent application Ser. No. 09/802,316, entitled CARDIAC RHYTHM MANAGEMENT SYSTEM USING TIME DOMAIN HEART RATE VARIABILITY INDICIA, filed on Mar. 8, 2001, which is incorporated by reference herein in its entirety, including its description of determining indications of patient wellness. In one example, telemetry interface device 510 is used to communicate an alert to a doctor or other caregiver using remote user interface 115 when the patient becomes unwell, such as when a patient wellness indicator crosses a predetermined threshold value. In one example, a QT interval length obtainable from a cardiac signal is used as a patient wellness indicator, and telemetry interface device 510 alerts a physician at remote user interface 115 when the QT interval length exceeds a predetermined threshold value or exhibits QT alternans (i.e., a pattern of successive alternating long-short QT intervals).

In yet another example in which device 505 regularly transmits to telemetry interface device 510 physiological information (e.g., electrogram information about one or more cardiac signals sensed at one or more patient electrodes, and/or information from one or more physiological sensors such as an accelerometer, a minute ventilation sensor, etc.), telemetry interface device 510 processes the physiological data to predict whether a future arrhythmia is likely to occur. This information is then either transmitted from telemetry interface device 510 to remote user interface 115 via far-field RF communication link 155, such as to notify a physician or other caregiver, and/or is transmitted back to implanted device 505 to trigger therapy that prevents the arrhythmia from occurring. One example of processing physiological and/or sensor data to predict and/or prevent an arrhythmia is described in Sweeney et al. U.S. Pat. No. 6,272,377, entitled CARDIAC RHYTHM MANAGEMENT SYSTEM WITH ARRHYTHMIA PREDICTION AND PREVENTION, which is incorporated by reference herein in its entirety, including its description of providing arrhythmia prediction and prevention techniques.

Figure 6:
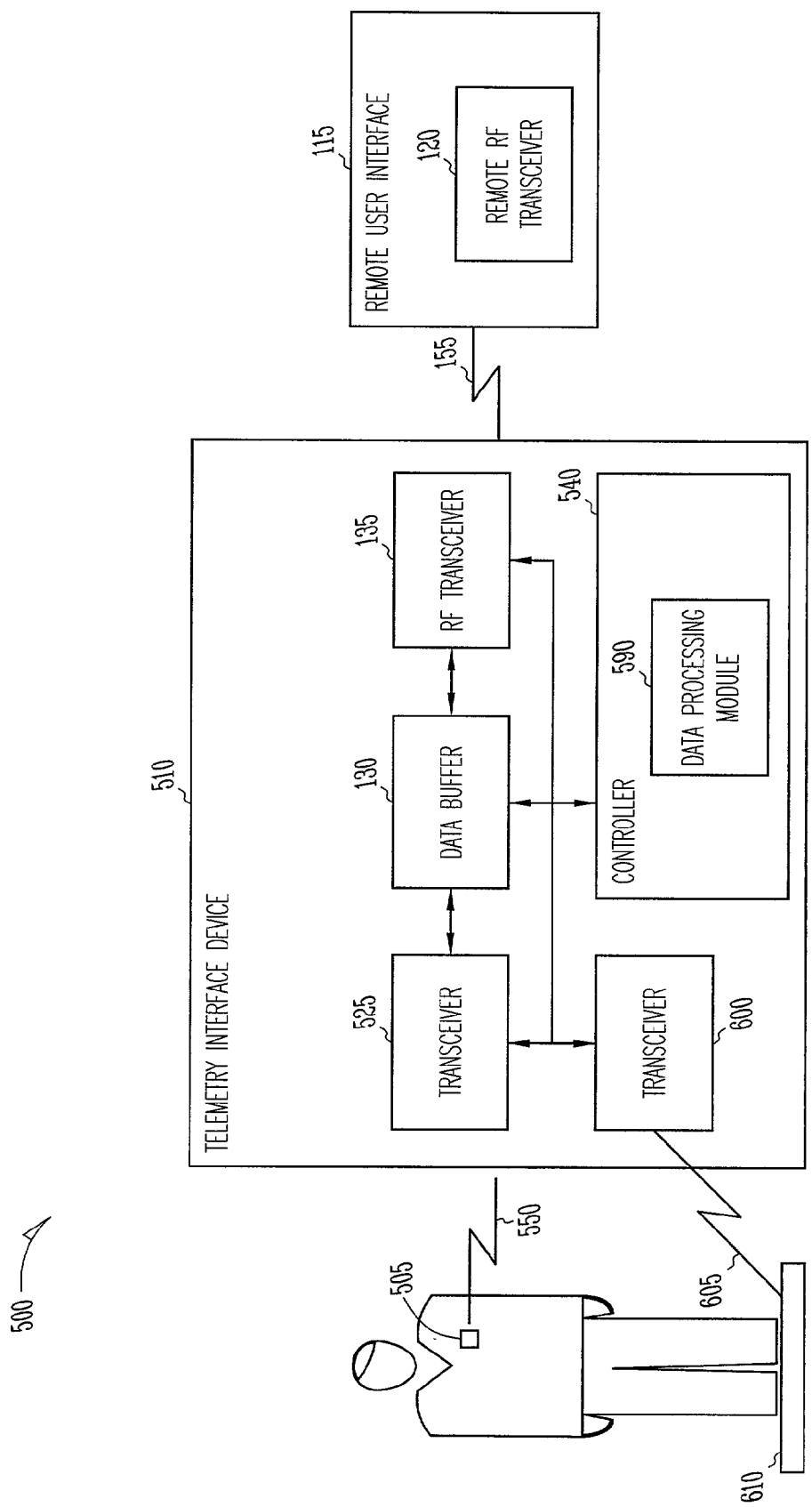
FIG. 6 is a schematic/block diagram illustrating another example of a telemetry interface device that, in addition to transceiving a communication signal from an implantable medical device, also transceives a communication signal from another device, such as an external sensor, associated with or used by the patient.

FIG. 6 is a schematic/block diagram illustrating another example of a telemetry interface device 510 that, in addition to transceiving a communication signal from an implantable device 505, also transceives a communication signal with another device 610 (such as an external sensor) associated with or used by the patient. In this example, telemetry interface device 510 includes a transceiver 600 for transceiving a communication signal, at 605, from another device 610 associated with or used by the patient. In one example, device 610 is a scale including a far-field RF transceiver communicating, at 610, information about the patient's weight to far-field RF transceiver 600 in telemetry interface device 510. Telemetry interface device communicates this information and information from implantable device 505 to remote far-field RF transceiver 120. Other examples of device 610 include an external pressure sensor (e.g., a cuff on the patient's finger), an external respiration monitor, or any other sensor providing information about the patient. By communicating information from both implantable device 505 and external device 610 to remote user interface 115, telemetry interface device 510 enhances the information available to the physician or other caregiver using remote user interface 115. Telemetry interface device 510 may further perform processing, using data processing module 590, of data from both implantable device 505 and external device 610 that includes correlating data from both of these sources. This also further enhances the information available to the physician or other caregiver using remote user interface 115. In one example, transceiver 600 is shared or combined with one of transceivers 525 or 135.

It is to be understood that the above description is intended to be illustrative, and not restrictive. For example, the above-discussed embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, the terms "first," "second," "third," etc. are used merely as labels, and are not intended to impose numeric requirements on their objects.

What is claimed is:

1. An external telemetry interface device to assist in communication between an implantable medical device to be implanted in a patient the implantable medical device carrying an inductive element and an external remote first far-field radio-frequency (RF) transceiver, the telemetry interface device including:
an inductive transceiver, configured to be communicatively coupled to the inductive element in the implantable medical device via a mutual inductance therebetween;
a second far-field RF transceiver, configured to be communicatively coupled to the remote first far-field RF transceiver;
a data buffer, coupled to the inductive and second far-field RF transceivers, to store data from the inductive and second far-field RF transceivers; and
a controller, coupled to the inductive and second far-field RF transceivers and the data buffer, to issue control signals directing communication by the inductive and second far-field RF transceivers using data from the data buffer, the controller including a data nrocessing module to alter or remove a first header from data received from the implantable medical device and to provide a different second header to data to be provided to the remote first far-field transceiver.

2. The device of claim 1, further including a power source.

3. The device of claim 2, in which the power source includes a battery.

4. The device of claim 3, in which the battery is rechargeable.

5. The device of claim 1, in which the controller includes a data processing module.

6. The device of claim 5, in which the data processing module is configured to execute instructions compressing data in the data buffer.

7. The device of claim 5, in which the data processing module is configured to execute instructions to obtain extracted information, from electrogram data received from the implanted device, for transmission byte second far-field RF transceiver to the remote first far-field RF transceiver.

8. The device of claim 7, in which the extracted information includes heart rate information.

9. The device of claim 7, in which the extracted information includes cardiac signal morphology information.

10. The device of claim 7, in which the extracted information includes times associated with intervals between heart depolarizations in the electrogram data.

11. The device of claim 7, in which the extracted information includes an alert condition relating to the patient's condition.

12. The device of claim 1, in which at least one of the inductive transceiver, the second far-field RF transceiver, and a third far-field RF transceiver is configured to be communicatively coupled to an external device associated with the patient.

13. An external telemetry interface device to assist in communication between an implantable medical device to be implanted in a patient and a remote far-field radio-frequency (RF) transceiver, the telemetry interface device including:
a first transceiver, configured to be communicatively coupled to the implantable medical device;
a second transceiver, configured to be communicatively coupled to the remote far-field RF transceiver;
a data buffer, coupled to the first and second transceivers, to store data from the first and second transceivers; and
a controller, coupled to the first and second transceivers and the data buffer, to issue control signals directing communication by the first and second transceivers using data from the data buffer, the controller including a data processing module configured to execute instructions to externally extract physiologic information, from electrogram data received from the implanted device via the first transceiver, for transmission by the second transceiver to the remote tar-field RF transceiver.

14. The device of claim 13, in which the extracted information includes heart rate information.

15. The device of claim 13, in which the extracted information includes cardiac signal morphology information.

16. The device of claim 13, in which the extracted information includes times associated with intervals between heart depolarizations in the electrogram data.

17. The device of claim 13, in which the extracted information includes an alert condition relating to the patient's condition.

18. The device of claim 13, in which at least one of the first transceiver, the second transceiver, and a third transceiver is configured to be communicatively coupled to an external device associated wit the patient.

19. A method of communicating between an implantable medical device to be implanted in a patient and an external remote far-field RF transceiver, the method including:
transceiving with the implantable medical device an inductively-coupled first communication signal, the transceiving with the implantable medical device including using an intermediary external transceiver that is separate from the external remote far-field RF transceiver;
transceiving with the external remote far-field RF transceiver a second communication signal, the transceiving with the external remote far-field RF transceiver including using the intermediary external transceiver; and
externally buffering data received from at least one of the first and second communication signals, the externally buffering data including removing or altering a first header on data received from the implantable device and providing a different second header on data to be provided to the external remote far-field transceiver.

20. The method of claim 19, further including compressing data from at least one of the first and second communication signals.

21. The method of claim 19, farther including extracting information from electro grain data included in the first communication signal.

22. The method of claim 19, further including extracting heart rate information from the first communication signal.

23. The method of claim 19, further including extracting cardiac signal morphology information from the first communication signal.

24. The method of claim 19, further including extracting from the first communication signal time intervals between heart depolarizations.

25. The method of claim 19, further including:
extracting information from electro gram data included in the first communication signal;
processing the extracted information to determine whether an alert condition is present; and communicating the alert condition to the external remote far-field RF transceiver if the alert condition is present.

26. The method of claim 19, further including transceiving, with an external device associated with the patient, a third communication signal.

27. A method of communicating between an implantable medical device that is implanted in a patient and an external remote far-field RF transceiver, the method including:
transceiving with the implantable medical device a first communication signal;
externally extracting physiologic information from electrogram data included in the first communication signal, the extracting using an intermediary external device that is separate from the external remote far-field RF transceiver; and
externally transceiving with the external remote far-field RF transceiver a second communication signal that includes information that is based on the physiologic information that was externally extracted from the electrogram data included in the first communication signal.

28. The method of claim 27, further including externally buffering data received from at least one of the first and second communication signals.

29. The method of claim 27, further including:
externally processing the extracted information to determine whether an alert condition is present; and
communicating the alert condition to the external remote far-field RF transceiver if the alert condition is present.

30. The method of claim 27, further including transceiving, with an external device associated with the patient, a third communication signal.

31. A method of communicating between an implantable medical device to be implanted in a patient and an external remote transceiver, the method including:
transceiving with the implantable medical device a first communication signal, the transceiving with the inhabitable medical device including using an intermediary external transceiver that is separate from the external remote transceiver,
externally processing the first communication signal to generate a second communication signal, the externally processing including removing or altering a first header on data received in the first communication signal and providing a different second header on data to be provided in the second communication signal; and
transceiving with the external remote transceiver the second communication signal, the transceiving with the external remote transceiver including using the intermediary external transceiver.

32. The method of claim 31, in wish the processing includes translating between a first communication protocol of the first communication signal and a different second communication protocol of the second communication signal.

33. The method of claim 31, in which the processing includes compressing data in the first communication signal and including the compressed data in the second communication signal.

34. The method of claim 31, in which the processing includes combining data from the implantable medical device with data received from another sensor associated with the patient and including the combined data in the second communication signal.

35. An external intermediary telemetry interface device to assist in communication between an implantable medical device to be implanted in a patient and a remote external transceiver, the external intermediary telemetry interface device separate from the remote external transceiver and including:
an external first transceiver, configured to be communicatively coupled to the implantable medical device to transceive a first communication signal;
an external RF second transceiver, configured to be communicatively coupled to the remote transceiver to transceive a second communication signal; and
an external controller, coupled to the first and second transceivers, the controller including a signal processor to process the first communication signal from the first transceiver to remove or alter a first header and provide the resulting second communication signal with a different second header to the second transceiver.

36. The device of claim 35, in which the signal processor is configured to translate between a first communication protocol of the first communication signal and a different second communication protocol of the second communication signal.

37. The device of claim 35, in which the signal processor is configured to compress data in the first communication signal, and to include the compressed data in the second communication signal.

38. The device of claim 35, in which the signal processor is configured to combine data from the implantable medical device with data received from another sensor associated with the patient, and to include the combined data in the second communication signal.

* * * * *

UNITED STATES PATENT AND TRADEMARK OFFICE
CERTIFICATE OF CORRECTION

PATENT NO.       : 7,060,030 B2
APPLICATION NO. : 10/041725
DATED            : June 13, 2006
INVENTOR(S)      : Von Arx et al.

It is certified that error appears in the above-identified patent and that said Letters Patent is hereby corrected as shown below:

In column 9, line 4, In Claim 1, delete "patient" and insert -- patient, --, therefor.

In column 9, line 22, In Claim 1, delete "nrocessing" and insert --processing --, therefor.

In column 9, line 40, In Claim 7, delete "byte" and insert -- by the --, therefor.

In column 10, line 11, In Claim 13, delete "tar-field" and insert -- far-field --, therefor.

Signed and Sealed this

Nineteenth Day of September, 2006

JON W. DUDAS
*Director of the United States Patent and Trademark Office*